(12) United States Patent
Arai

(10) Patent No.: US 7,128,926 B2
(45) Date of Patent: Oct. 31, 2006

(54) ESTER COMPOUND AND USE THEREOF

(75) Inventor: Tomonori Arai, Iwate (JP)

(73) Assignee: Incorporated Administrative Agency, National Agriculture and Bio-Oriented Research Organization, Tsukuba (JP)

( * ) Notice: Subject to any disclaimer, the term of this patent is extended or adjusted under 35 U.S.C. 154(b) by 0 days.

(21) Appl. No.: 10/534,522

(22) PCT Filed: Nov. 11, 2003

(86) PCT No.: PCT/JP03/14303

§ 371 (c)(1),
(2), (4) Date: May 11, 2005

(87) PCT Pub. No.: WO2004/043896

PCT Pub. Date: May 27, 2004

(65) Prior Publication Data

US 2006/0039940 A1    Feb. 23, 2006

(30) Foreign Application Priority Data

Nov. 12, 2002  (JP)  ............................. 2002-328482

(51) Int. Cl.
| A61N 25/00 | (2006.01) |
|---|---|
| A61N 37/00 | (2006.01) |
| A61N 37/02 | (2006.01) |
| A61N 37/06 | (2006.01) |
| C07C 69/52 | (2006.01) |
| A61K 31/21 | (2006.01) |
| A61K 31/215 | (2006.01) |
| A61K 31/22 | (2006.01) |

(52) U.S. Cl. .................. 424/405; 514/506; 514/529; 514/546; 514/549; 560/205; 560/220; 560/225

(58) Field of Classification Search ............... 424/405; 514/506, 529, 546, 549; 560/205, 220
See application file for complete search history.

(56) References Cited

FOREIGN PATENT DOCUMENTS

| JP | 55-122739 | 9/1980 |
|---|---|---|
| JP | 57-021348 | 2/1982 |

OTHER PUBLICATIONS

Nakahata et al. Biosci. Biotechnol. Biochem. 2003, 67(12), 2627-2631.*
Arai et al. Journal of Chemical Ecology 2003, 29(10), 2213-2223.*
Arai Appl. Entomol. Zool. 2000, 35(4), 525-528.*
Barbara A. Bierl-Lleonhardt, Daniel S. Moreno, Meyer Schwarz, JoAn Fargerlund, and Jack R. Plimmer 'Isolation, Identification and Synthesis of the Sex Pheromone of the Citrus Mealybug, Planococcus Citri (Risso)', Tetrahedron Letters, vol. 22, pp. 389 to 392, 1981.

* cited by examiner

Primary Examiner—Johann Richter
Assistant Examiner—Ernst V. Arnold
(74) Attorney, Agent, or Firm—Oblon, Spivak, McClelland, Maier & Neustadt, P.C.

(57) ABSTRACT

It is an object of the present invention to provide a novel ester compound and the use thereof as a sex attractant. The present invention provides a compound represented by formula (I) described below, and a sex attractant comprising, as an active ingredient, this compound:

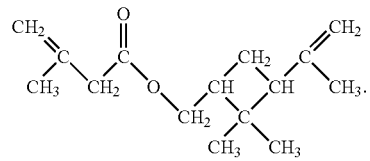

5 Claims, 3 Drawing Sheets

ESTER COMPOUND AND USE THEREOF

TECHNICAL FIELD

The present invention relates to a novel ester compound and a sex attractant containing the above compound as an active ingredient.

BACKGROUND ART

*Pseudococcus cryptus* is the most important insect pest growing in Japanese citrus fruits, which causes enormous damage to greenhouse culture such as the culture of hothouse oranges. *Pseudococcus cryptus* has a strong characteristic that it hides at an indistinctive site such as a space between leaves, and thus, it is difficult to find the presence thereof when the insect pests exist at a low density. Since the control of these insect pests is carried out after the pests have caused certain damage, the control may be too late to start in many cases. Thus, it is an urgent issue to efficiently forecast of emergence of the insect pests.

In general, many scale insects including *Pseudococcidae* have the form of an adult insect that is significant different between males and females. An adult male has wings for flying, but its life time is extremely short, such as a duration of life between several hours to 1 day. In contrast, an adult female does not have such wings and thus does not have high migration ability, but it has a longer life time than an adult male. Accordingly, an adult male should find an adult female to mate it within a limited period of time. In order to efficiently find females, some scale insects utilize their sex pheromone. In recent years, identification of pheromones of scale insects has progressed, and the structures and components of pheromones of several scale insects have been identified (e.g. *Planococcus citri, Pseudococcus comstocki, Planococcus ficus, Aonidiella aurantii, Aonidiella citrina, Comstockaspis perniciosa, Pseudaulacaspis pentagona,* 5 types belonging to *Matsucoccus*, etc. (please refer to Non-Patent Documents 1 to 12)).

On the other hand, studies regarding agents or techniques for controlling insects utilizing sex pheromones of the insects, such as mass trapping or communication disruption between males and females, have actively been conducted. In these methods, using sex pheromone, adult males are attracted to a certain place, and the attracted insects are then captured and killed. Otherwise, a normal mating action between males and females is artificially disturbed to reduce the population of the next generation, thereby controlling insect pests. In addition, it is also possible to forecast the development of insect pests that are targets of control, using such sex pheromone. It is considered that the control of insect pests using sex pheromone is an eco-friendly technique, which reduces burden on the environment. It is anticipated that such a technique will be developed for more types of insect pests in future.

Under such circumstances, as a result of studies regarding the ecology of *Pseudococcus cryptus* and its natural enemy, the present inventors have found for the first time that *Pseudococcus cryptus* also has sex pheromone.

[Patent Document 1]
JP Patent Publication (Kokoku) No. 61-036738 B (1986)

[Non-Patent Document 1]
Bierl-Leonhardt B. A., D. S. Moreno, M. Schwarz, H. S. Forster, J. R. Plimmer and E. D. DeVilbiss (1980) Identification of the pheromone of the comstock mealybug. Life Science 27: 399–402.

[Non-Patent Document 2]
Bierl-Leonhardt B. A., D. S. Moreno, M. Schwarz, J. Fargerlund and J. R. Plimmer (1981) Isolation, identification and synthesis of the sex pheromone of the citrus mealybug, *Planococcus citri* (Risso). Tetrahedr. Lett. 22: 389–392.

[Non-Patent Document 3]
Dunkelblum E., Z. Mendel, F. Assael, M. Harel, L. Kerhoas and J. Einhorn (1993) Identification of the female sex pheromone of the Israeli pine bast scale *Matsucoccus josephi*. Tetrahedr. Lett. 34:2805–2808.

[Non-Patent Document 4]
Einhorn J., P. Menassieu, C. Malosse and P. Ducrot (1990) Identification of the sex pheromone of the maritime pine scale *Matsucoccus feytaudi*. Tetrahedr. Lett. 31: 6633–6636.

[Non-Patent Document 5]
Gieselmann M. J., D. S. Moreno, J. Fargerlund, H. Tashiro and W. L. Roelofs (1979a) Identification of the sex pheromone of the yellow scale. J. Chem. Ecol. 5: 27–33.

[Non-Patent Document 6]
Gieselmann M. J., R. E. Rice, R. A. Jones and W. L. Roelofs (1979b) Sex pheromone of the San Jose scale. J. Chem. Ecol. 5:891–900.

[Non-Patent Document 7]
Heath R. R., J. R. McLaughlin, J. H. Tumlinson, T. R. Ashley and R. E. Doolittle (1979) Identification of the white peach scale sex pheromone: An illustration of micro techniques. J. Chem. Ecol. 5:941–953.

[Non-Patent Document 8]
Hinkens D. M., J. S. McElfresh and J. G. Millar (2001) Identification and synthesis of the sex pheromone of the vine mealybug, *Planococcus ficus*. Tetrahedr. Lett. 42: 1619–1621.

[Non-Patent Document 9]
Lanier G. N., Y. Qi, J. R. West, S. C. Park, F. X. Webstar and R. M. Silverstein (1989) Identification of the sex pheromone of three *Matsucoccus* pine bast scales. J. Chem. Ecol. 15: 1645–1659.

[Non-Patent Document 10]
Negishi T., M. Uchida, Y. Tamaki, K. Mori, T. Ishiwatari, S. Asano and K. Nakagawa (1980) Sex pheromone of the comstock mealybug, *Pseudococcus comstocki* Kuwana: Isolation and identification. Appl. Entomol. Zool. 15: 328–333.

[Non-Patent Document 11]
Roelofs W., M. Gieselmann, A. Carde, H. Tashiro, D. S. Moreno, C. A. Henrick and R. J. Anderson (1977) Sex pheromone of the California red scale, *Aonidiella aurantii*. Nature 267: 698–699.

[Non-Patent Document 12]
Roelofs W., M. Gieselmann, A. Carde, H. Tashiro, D. S. Moreno, C. A. Henrick and R. J. Anderson (1978) Identification of the California red scale sex pheromone. J. Chem. Ecol. 4: 211–224.

DISCLOSURE OF THE INVENTION

It is an object of the present invention to provide a novel ester compound and a sex attractant containing the above compound as an active ingredient.

In order to achieve the aforementioned object under the current circumstances, the present inventors have conducted intensive studies directed towards searching for the sex pheromone of *Pseudococcus cryptus* belonging to *Pseudo-*

*coccidae*. As a result, they have succeeded in isolating the sex pheromone and determining the structure thereof. Thus, they have discovered the properties of the sex pheromone of *Pseudococcus cryptus* and the fact that the pheromone component is 3-isopropenyl-2,2-dimethylcyclobutylmethyl 3-methyl-3-butenoate, thereby completing the present invention.

That is to say, the present invention includes the following features:

(1) A compound represented by the following formula (I):

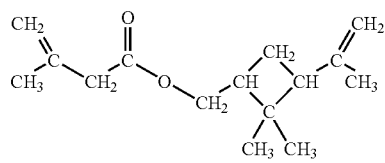

(2) A sex attractant comprising the compound represented by the above-described formula (I) as an active ingredient.

The compound represented by the above-described formula (I) can be obtained by extraction and purification from *Pseudococcus cryptus*.

As an extracting solvent used herein, organic solvents may generally be used. Preferred examples may include: water-miscible organic solvents such as methanol, ethanol, propanol, or acetone; and water-immiscible organic solvents such as ether, ethyl acetate, chloroform, pentane, or hexane. The obtained extract is concentrated and purified, so as to efficiently obtain an ester compound of interest.

Purification can be carried out by appropriately combining silica gel chromatography, reverse phase silica gel chromatography, adsorption chromatography, reverse phase adsorption chromatography, gas chromatography, high performance liquid chromatography, reverse phase high performance liquid chromatography, and the like.

The thus obtained ester compound exhibits an action to sexually attract *Pseudococcus cryptus*, and thus, it can be used as a sex attractant.

In order to use the compound of the present invention as a sex attractant, the above-described ester compound may directly be contained in a trap. However, in general, the above-described ester compound is dissolved in a suitable organic solvent such as pentane, hexane, diethyl ether, acetone, methylene chloride, or the like, and the obtained product is then encapsulated in a rubber cap, a capillary, a plastic capsule, or the like. Alternatively, the above product is carried and adsorbed on an activated carbon, an inactivated powder such as silica gel, or a granule, and it is then used. The amount and usage of the compound of the present invention as a sex attractant are not limited. Generally, the compound of the present invention is contained in a sex attractant as prepared above at an order of ng. This sex attractant is placed in a trap onto which an adhesive substance or the like has been applied. Thereafter, such a trap may be established for every 2 or 3 trees in the orchard. Thus, adult males of *Pseudococcus cryptus* are attracted to the compound of the present invention and are eventually captured by the trap onto which the adhesive substance has been applied.

Figure 1:
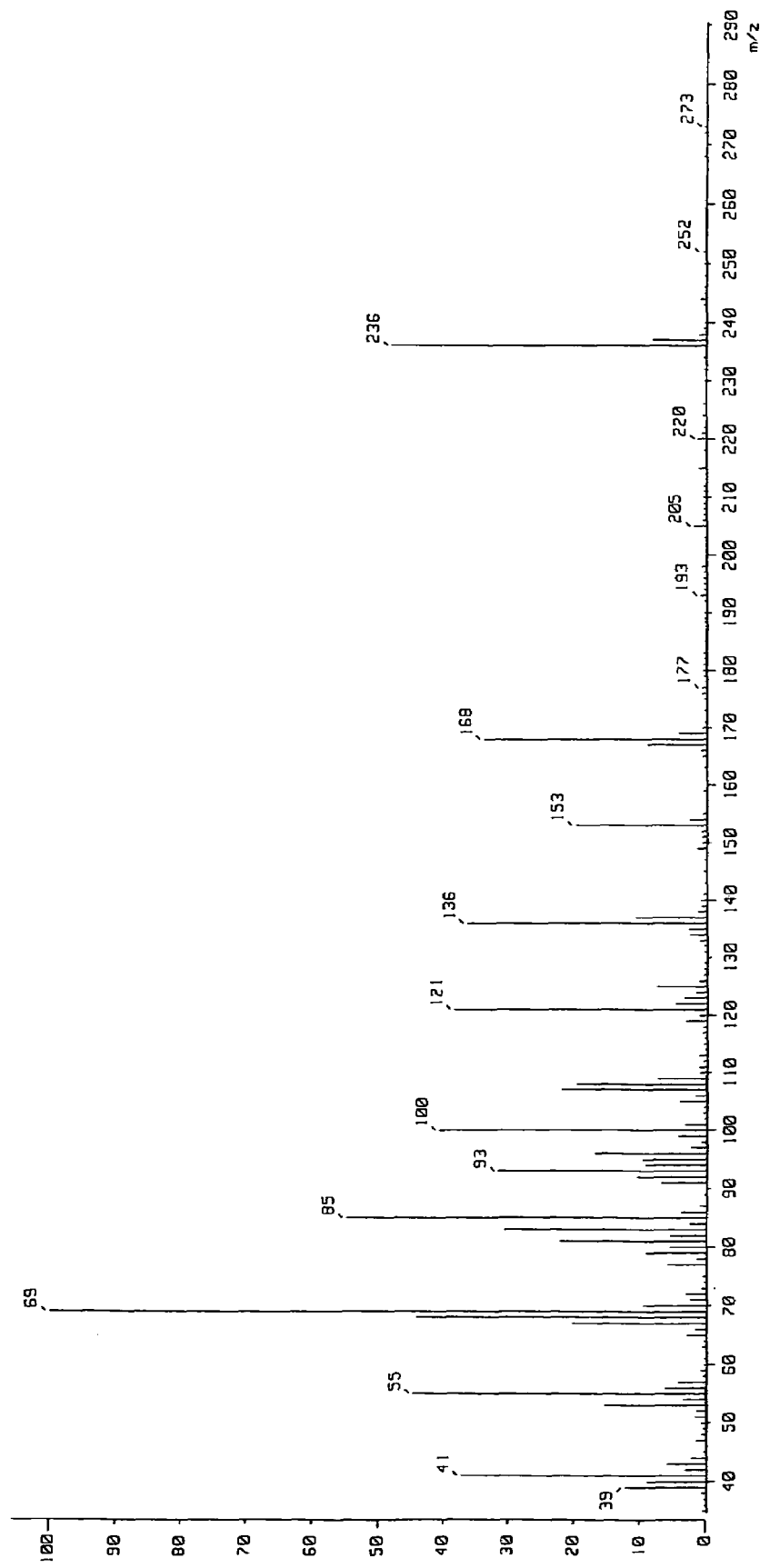
FIG. 1 shows a mass spectrum of an active ingredient of sex pheromone of *Pseudococcus cryptus;*

The present specification includes part or all of the contents as disclosed in the specification and/or drawings of JP Patent Application No. 2002-328482, which is a priority document of the present application.

BEST MODE FOR CARRYING OUT THE INVENTION

The present invention will be more specifically described in the following examples. However, the examples are not intended to limit the scope of the present invention.

EXAMPLE 1

(1) Isolation Operation

Extraction of Sex Pheromone

A pumpkin inoculated with 500 to 4,000 virgin females of *Pseudococcus cryptus* was placed in a 5-liter double-capped desiccator. Thereafter, pheromone accumulated in the desiccator was captured with 1 g of an adsorbent (Tenax GC). The period of time for capturing such pheromone was set at approximately 30 days. The capturing time was set at 7 hours per day, and the flow rate of the air was set at 7 liters per minute. The pheromone captured by the absorbent was extracted with 40 ml of pentane at a rate of once every 3 days. In order to estimate the amount of pheromone captured, dead insects were removed every 3 or 4 days, and virgin females were replenished. The collected extract (400 ml) was subjected to vacuum concentration at room temperature, and the obtained concentrate (10 ml) was defined as a crude extract of sex pheromone of *Pseudococcus cryptus*.

Purification of Sex Pheromone

Subsequently, using the activity of attracting adult males of *Pseudococcus cryptus* as an indicator, sex pheromone was purified from the above-described crude extract. First, a sex pheromone crude extract (2 ml) obtained by subjecting vacuum concentration again was fractionated by chromatography using a column filled with 30 g of florisil (containing 7% water, 100–200 meshes, Floridin Co.). Elution was carried out using a mixed solution consisting of diethyl ether and hexane. Extraction was successively carried out using 50 ml of hexane, 120 ml of 5% ether/hexane, 150 ml of 15% ether/hexane, 150 ml of 25% ether/hexane, and 150 ml of 50% ether/hexane. Thereafter, a 5% ether/hexane fraction (120 ml) exhibiting the highest attracting activity was subjected to vacuum concentration. The thus concentrated fraction (10 ml) was purified by high performance liquid chromatography (hereinafter referred to as HPLC) (HEWLETT PACKARD SERIES 1050). In HPLC, a silica gel column (Inertsil, 5 µm, 4.6 mm I.D.×250 mm, GL Science Inc.) was used, and elution was carried out using a solvent with a composition of 3% ether/hexane at a flow rate of 1 ml/min. In HPLC, a fraction (0.5 ml) with a retention time of 7.5 to 8 minutes exhibited the highest attracting activity. This fraction and the next fraction (a fraction (0.5 ml) with a retention time of 8 to 8.5 minutes) were gathered, and the gathered fraction was then fractionated by gas chromatography (hereinafter referred to as GC). As a GC device, HEWLETT PACKARD 5890 SERIES II was used, and as a column, FFAP (0.56 mm I.D.×15 m, a liquid phase thickness of 1 µm, GL Science Inc.) was used. Helium was used as a carrier gas, and the flow rate was set at 5 ml/min. Conditions for the temperature of an oven were set such that a temperature of 50° C. was retained for 1 minute and then the temperature was increased up to 220° C. at a rate of 5° C./min. In GC, a fraction with a retention time of 20.5 to 21 minutes exhibited the highest attracting activity (please refer to Table 1 shown below). The above-described extraction and purification process was repeatedly carried out, so as to obtain 3 ml of purified sex pheromone (500,000 female-day equivalents/300 ml). In the present specification, the term "500,000 female-day equivalents" is used to mean the amount of pheromone released from 500,000 adult females per day.

TABLE 1

Activities of Florisil LC, HPLC, GC fractions of attracting adult males of *Pseudococcus cryptus*

| Fraction | Rate of attracting adult males (%)[a] | | Significant difference[c] |
|---|---|---|---|
| | Treated group[b] | Control group | |
| Florisil | | | |
| Hexane | 2.1 | 10.8 | n.s. |
| 5% E/H | 76.5 | 0 | ** |
| 15% E/H | 54.4 | 2.1 | * |
| 25% E/H | 56.7 | 4.1 | n.s. |
| 50% E/H | 50.7 | 7.5 | * |
| HPLC | | | |
| 0–7 minutes | 20.1b | 3.0 | n.s. |
| 7–10 minutes | 80.5a | 0 | ** |
| 10–16 minutes | 66.6a | 37 | * |
| Blank | 60.0a | 0 | ** |
| HPLC 7–10 minutes | | | |
| 7–7.5 minutes | 12.1b | 4.2 | n.s. |
| 7.5–8 minutes | 74.8a | 0 | ** |
| 8–8.5 minutes | 60.0ab | 0 | ** |
| 8.5–10 minutes | 62.0ab | 0 | ** |
| GC | | | |
| 0–15 minutes | 3.0b | 0 | n.s. |
| 15–18 minutes | 2.6b | 5.6 | n.s. |
| 18–19.5 minutes | 3.0b | 0 | n.s. |
| 19.5–20 minutes | 22.5b | 0 | ** |
| 20–20.5 minutes | 5.6b | 6.1 | n.s. |
| 20.5–21 minutes[d] | 79.6a | 1.5 | ** |
| Blank | 16.7b | 0 | n.s. |

[a]The total value obtained by repeating the process 3 times
[b]There are no significant differences among the same characters (Tukey-Kramer-test, p = 0.05).
[c]The codes * and ** indicate that males were attracted to the treated fraction group more strongly than to the control group at standards of 5% and 1%, respectively. The code n.s. indicates that no differences were observed between both groups in terms of the attracting rate (t-test).
[d]The total value obtained by repeating the process 5 times (2) Structure Determination Analysis of Structure of Pheromone The purified attracting active ingredient was analyzed with a gas chromatography-mass spectrometer (hereinafter referred to as GC-MS) in terms of the molecular weight and molecular structure thereof (wherein an JEOL SX-102A double-focusing mass-spectrometer manufactured by JEOL was used as an MS apparatus for GC-MS). HEWLETT PACKARD 5890 SERIES II was used as a GC apparatus for GC-MS, and FFAP (0.25 mm I.D.×30 m, a liquid phase thickness of 0.25 μm, GL Science Inc.) was used as a column. Helium was used as a carrier gas, and the flow rate was set at 1 ml/min. Conditions for the temperature of an oven were set such that a temperature of 80° C. was retained for 1 minute and then the temperature was increased up to 210° C. at a rate of 7° C./min. An ionization potential was 70 eV, and an ionization current was 300 μA. Isobutane gas was used as reaction gas in the measurement at a CI mode.

The isolated active ingredient had a retention time of 14.73 minutes in GC-MS. The active ingredient showed a peak with such characteristics as M/e: 69 (100%), 236 (8%), 168 (26%), 136 (22%), and 100 (32%) in an EI mass spectrum. The mass number was estimated to be 236 from a CI mass spectrum. In addition, as a result of high-resolution measurement, the mass number was calculated to be 236.1808, and the elemental composition was estimated to be $C_{15}H_{24}O_2$. The retention time of a hydrogenation product of the isolated active ingredient was 13.35 minutes. This product showed a peak with such characteristics as M/e: 83 (100%), 170 (25%), 143 (12%), 123 (10%), and 98 (69%) in an EI mass spectrum. The mass number of the hydrogenation product was estimated to be 240 from a CI mass spectrum, and it was assumed that it has two double bond structures.

Analysis of Alcohol Moiety of Active Ingredient

Further, in order to determine the structure of an alcohol moiety of the isolated active ingredient, the active ingredient was subjected to alkaline hydrolysis and acetylation. 0.5 N KOH (2 ml) was added to a portion (0.1 ml) of the isolated active ingredient, and the mixture was left overnight. Thereafter, it was extracted with hexane (4 ml×3 times). Acetic anhydride (1 ml) was added to a hexane fraction (0.1 ml) obtained by vacuum concentration, and the mixture was then left overnight. Thereafter, it was extracted with hexane (4 ml×3 times).

The hydrolysate of the isolated active ingredient was subjected to GC-MS analysis. As a result, a substance having a retention time of 12.63 minutes and the number of mass of 154 that was estimated from a CI mass spectrum, was detected in neutral and basic fractions. This substance showed a peak with such characteristics as M/e: 71 (100%), 139 (12%), 123 (9%), and 121 (27%) in an EI mass spectrum. Accordingly, it was assumed that the active ingredient isolated by the above-described purification was an ester consisting of alcohol with a molecular weight of 154 and acid with a molecular weight of 100.

Subsequently, the alcohol moiety of the isolated active ingredient was acetylated and then subjected to GC-MS analysis. As a result, the portion had a retention time of 10.63 minutes and showed a peak with such characteristics as M/e: 68 (100%), 196 (1.6%), 128 (20%), 121 (19%), and 86 (9%) in an EI mass spectrum. The number of mass was estimated to be 196 from a CI mass spectrum. The mass spectrum of this substance matched well with data regarding the sex pheromone of *Planococcus citri*. Moreover, it was found that this substance had activity of attracting adult males of *Planococcus citri* (please refer to Table 2 shown below). The level of such attracting activity was almost the same as those of the crude extract of sex pheromone of *Planococcus citri* and the acetylated alcohol moiety of sex pheromone of *Planococcus citri* (please refer to Table 3 shown below). Thus, it was strongly suggested that the acetylated alcohol moiety of the active ingredient isolated from *Pseudococcus cryptus* is a substance having a structure extremely similar to the sex pheromone of *Planococcus citri*, and that there is a possibility that the alcohol moiety of the active ingredient isolated from *Pseudococcus cryptus* is identical to the alcohol moiety of the sex pheromone of *Planococcus citri*.

Determination of Structure of Pheromone

Figure 2:
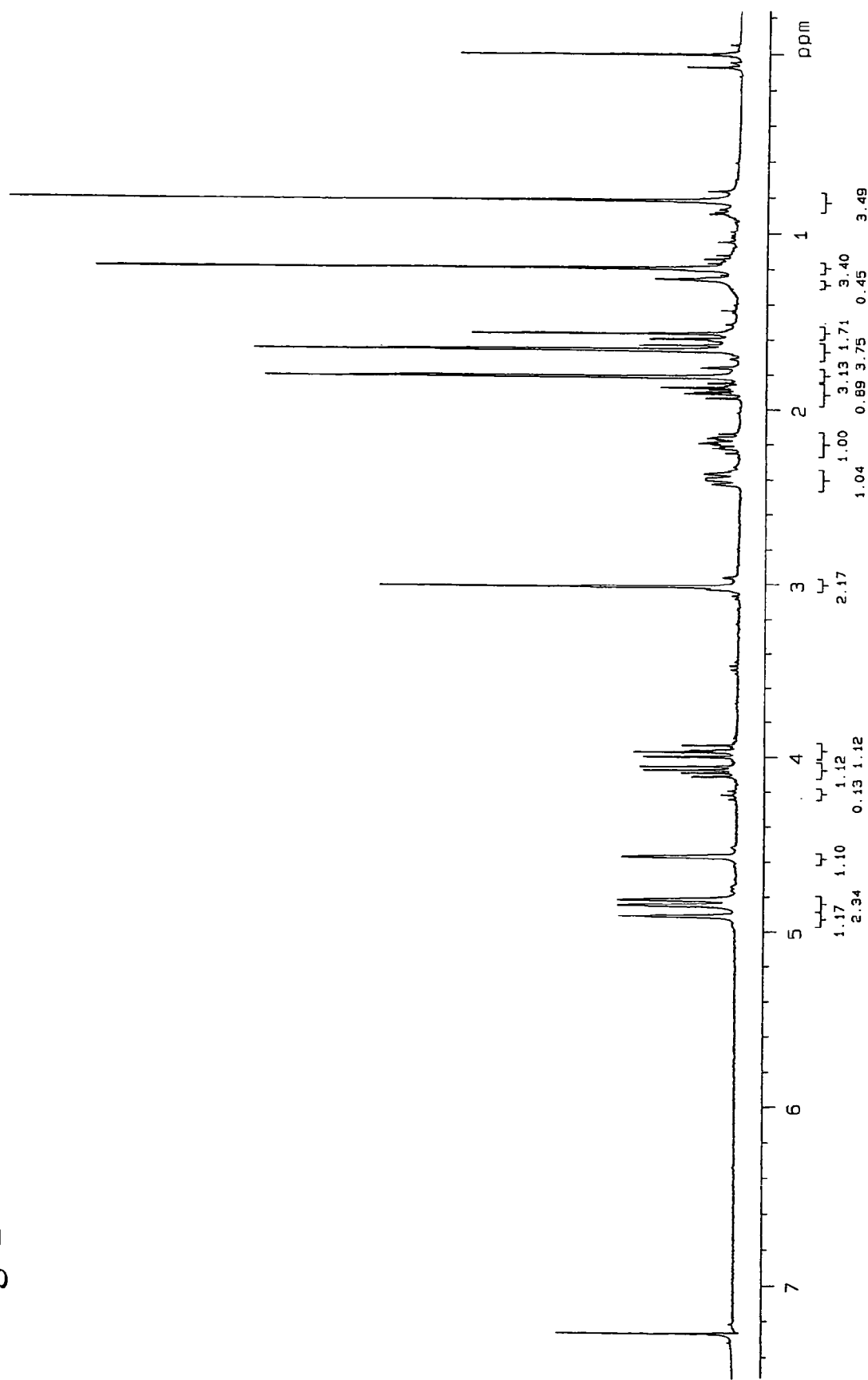
FIG. 2 shows a 600 MH$_z$ 1H NMR spectrum of an active ingredient of sex pheromone of *Pseudococcus cryptus.
Figure 3:
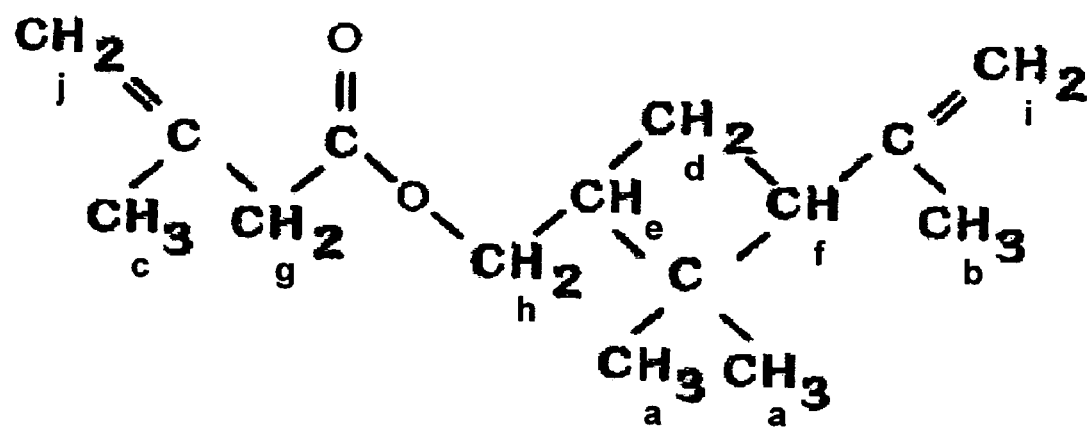
* and FIG. 3 is a view showing the configuration of hydrogen assigned by COSY analysis and HOHAHA analysis.

The isolated active ingredient was analyzed by GC-MS. As a result, a mass spectrum shown in FIG. 1 was obtained ([Mass Spectrum] Date: 19 Jun. 2002 14:11; Data: 7362007;

Sample: ryan; Note: Inlet: Direct; Ion mode: EI+; Spectrum Type: Normal Ion [MF-Linear]; RT: 0.87 min; Scan#: 52,54; BP: m/z 69.0000; Int.: 53.66; Output m/z range: 34.6247 to 290.4709; Cut Level: 0.00%; 594766). Moreover, the structure of the active ingredient was analyzed by COSY and HOHAHA measurements using a proton NMR (JEOL A600; $^1$H NMR 600 MH$_z$; JEOL). As a result, an NMR spectrum shown in FIG. 2 was obtained ([STANDARD 1H OBSERVE] Date: 18 Jun. 2002; Solvent: CDCl3; Ambient temperature; GEMINI-300 "varian"; PULSE SEQUENCE: Relax delay: 1.502 sec; Pulse 45.2 degrees Acq. time: 3.498 sec; width 4500.5 Hz; 16 repetitions; OBSERVE: H1, 300.1350720 MHz; DATA PROCESSING FT size 32768; Total time 1 minute). Hydrogen was assigned as shown in FIG. 3. From these results, it was determined that the structure of sex pheromone with activity of attracting adult males of *Pseudococcus cryptus* is represented by the following formula (I):

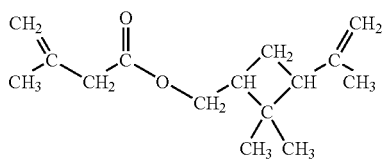

EXAMPLE 2

Sexual Attracting Activity

Biological Assay of Attracting Activity Using Petri Dish

Biological assay of sexually attracting activity shown in Tables 1 and 2 was carried out as follows. First, two square filter papers with an area of 1 cm² were placed on a Petri dish with a diameter of 90 mm. Thereafter, one paper was impregnated with each of sample solutions (shown in Tables 1 and 2) (100 μl of a stock solution in the case of each fraction shown in Table 1 and a crude extract shown in Table 2, and 10 μl of a stock solution in the case of an acetylated product shown in Table 2), and it was defined as a treated group. The other paper was impregnated with only a solvent (100 μl), and it was defined as a control group. Hexane was used as such a solvent. The papers were air-dried, and then, 10 to 20 adult males of *Pseudococcus cryptus* (in the biological assay shown in Table 1) or *Planococcus citri* (in the biological assay shown in Table 2) were released to the Petri dish. The Petri dish was then capped. Approximately 10 to 60 minutes later, when the movement of the males stopped, the presence or absence of attracting activity was confirmed from the ratio of males attracted to each filter paper. The results are shown in the aforementioned table and Table 2.

TABLE 2

Activities of the sex pheromone of *Planococcus citri* and the acetylated substances of each sex pheromone of attracting adult males of *Planococcus citri*

| Attracting source | Rate of attracting adult males (%)[a] | | Significant difference[b] |
| --- | --- | --- | --- |
| | Treated group | Control group | |
| Crude extract of sex pheromone of *Planococcus citri* | 52.8 | 0 | ** |
| Acetylated product 1[c] | 48.9 | 0 | ** |
| Acetylated product 2[d] | 56.9 | 0 | ** |

[a]The total value obtained by repeating the process 3 times
[b]The code ** indicates that the males were attracted to the treated group more strongly than to the control group at a standard of 0.01% (t-test, p = 0.0001).
[c]Acetylated product of sex pheromone of *Pseudococcus cryptus*
[d]Acetylated product of sex pheromone of *Planococcus citri*

Biological Assay of Attracting Activity Using a Pheromone Trap

Biological assay of sexually attracting activity shown in Table 3 was carried out as follows. First, a 1-cm² square filter paper, which had been impregnated with each of various attracting substances shown in Table 3 (100 μl of a stock solution in the case of crude sex pheromones shown in Table 3, and 10 μl of a stock solution in the case of acetylated products shown therein) and then air-dried, was attached to the center of a yellow adhesive trap (10 cm height×20 cm width). Thereafter, the trap was placed in a glass chamber with a size of 5 m×6.5 m. On the other hand, a filter paper impregnated with only a solvent (100 μl) was used as a control. The three traps were placed in a line at intervals of 1.4 m at a position of a height of 1.8 m. Of these, the trap (control) to which a filter paper impregnated with a solvent and then air-dried had been attached was placed in the center. Below the control, a tissue paper on which male pupa at a stage immediately before eclosion were attached was placed every day, so that newly emerged adult males were spontaneously provided from this tissue paper for the test. The traps were exchanged with new traps every morning, so that the number of adult males captured by the traps was examined. The results are shown in Table 3.

TABLE 3

The number of adult males of *Planococcus citri* captured by yellow adhesive traps to which various types of attracting substances were attached

| Attracting source | Mean value ± standard error (repetition) |
| --- | --- |
| Acetylated substance 1[a] | 133.3 ± 46.9(4)a[c] |
| Crude extract of sex pheromone of *Planococcus citri* | 114.8 ± 44.5(4)a |
| Control | 0.3 ± 0.3(4)b |
| Acetylated substance 2[b] | 59.4 ± 18.9(5)a |
| Crude extract of sex pheromone of *Planococcus citri* | 84.2 ± 26.2(5)a |
| Control | 0.6 ± 0.4(5)b |

[a]Acetylated product of sex pheromone of *Pseudococcus cryptus*
[b]Acetylated product of sex pheromone of *Planococcus citri*
[c]There are no significant differences among the same characters (Tukey-Kramer-test, p = 0.05).

All publications, patents and patent applications cited herein are incorporated herein by reference in their entirety.

INDUSTRIAL APPLICABILITY

The present invention provides a novel ester compound, which has an action to attract adult males of *Pseudococcus cryptus* and is useful as a sex attractant.

What is claimed is:

1. Isolated and purified 3-isopropenyl-2,2-dimethylcyclobutylmethyl 3-methyl-3-butenoate represented by the following formula (I):

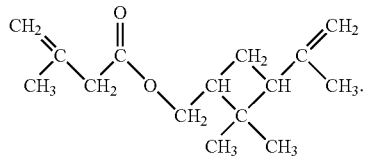

2. A sex attractant comprising, the isolated and purified 3-isopropenyl-2,2-dimethylcyclobutylmethyl 3-methyl-3-butenoate; and an organic solvent selected from the group consisting of pentane, hexane, diethyl ether, acetone, methylene chloride, and combinations thereof.

3. A sex attractant comprising, the isolated and purified 3-isopropenyl-2,2-dimethylcyclobutylmethyl 3-methyl-3-butenoate encapsulated in a rubber cap, a capillary, or a plastic capsule.

4. A sex attractant comprising, the isolated and purified 3-isopropenyl-2,2-dimethylcyclobutylmethyl 3-methyl-3-butenoate contained in a trap.

5. A sex attractant comprising, the isolated and purified 3-isopropenyl-2,2-dimethylcyclobutylmethyl 3-methyl-3-butenoate carried and absorbed on an activated carbon, an inactivated powder or a granule.

* * * * *